US007569222B2

(12) United States Patent
Woerly

(10) Patent No.: US 7,569,222 B2

(45) Date of Patent: Aug. 4, 2009

(54) HYDROGEL MEMBRANE COMPOSITION AND USE THEREOF

(76) Inventor: Stéphane Woerly, 1080 avenue des Érables, Apt. 202, Québec (CA) G1R 2N2

( * ) Notice: Subject to any disclaimer, the term of this patent is extended or adjusted under 35 U.S.C. 154(b) by 804 days.

(21) Appl. No.: 10/298,046

(22) Filed: Nov. 18, 2002

(65) Prior Publication Data

US 2004/0096505 A1 May 20, 2004

(51) Int. Cl.
*A01N 65/00* (2006.01)

(52) U.S. Cl. .................................................... 424/93.7

(58) Field of Classification Search ................. 424/400, 424/93.7; 514/17–20

See application file for complete search history.

(56) References Cited

U.S. PATENT DOCUMENTS

| | | | | | |
|---|---|---|---|---|---|
| 4,400,833 | A | | 8/1983 | Kurland | |
| 5,266,325 | A | * | 11/1993 | Kuzma et al. | 424/422 |
| 5,861,034 | A | | 1/1999 | Taira et al. | |
| 5,863,551 | A | * | 1/1999 | Woerly | 424/423 |
| 5,997,895 | A | | 12/1999 | Narotam et al. | |

OTHER PUBLICATIONS

CAS abstract of Vetvicka et al. CS 223295, obtained on Sep. 12, 2006 on CAPlus/STN, 2 pages.*

Taber's Cyclopedic medical Dictionary (1985) 15th ediction. Thomas, C. editor (F.A. Davis Company: Philadelphia, PA), pp. 474-475.*

Park et al. "Thermoreversible gel containing RGD sequence as a extracellular matrix" Proceedings of the International Symposium on Controlled Release of Bioactive Materials (2000), 27th, 249-250; CAS abstract only. Downloaded from the CAPLUS database on Jul. 15, 2007.*

Lukas et al. "Hydrogels for encapsulation of mammalian cells" Macromol. Symp. (Aug. 2001) 172: 157-165.*

Friends et al. "Hydrogels Based on Copolymers of N-(2-hydroxyethyl)methacrylamide, 2-Hydroxyethylmethacrylate and 4-t-buttyl-2-hydroxycyclohexyl methacrylate" J. Polymer Sci. (1993) 49: 1869-1876.*

McCulley et al., Corneal Endothelial Transplantation, Ophthalmology, Mar. 1980, vol. 87, No. 3, pp. 194-201.

Bhatia et al., A synthetic dural prosthesis constructed from hydroxyethylmethacrylate hydrogels, J Neurosurg, 1995; 83: 897-902.

Harat et al., Experimental evaluation of the net "Dalop" covered with collagen as the dural substitute, Zent. bl. Neurochir., 1989, 50: 145-148.

Laquerriere et al., Experimental evaluation of bilayered human collagen as a dural substitute, J. Neurosurg., 1993, 78(3): 487-491.

Maurer et al., Vicryl (polyglactin 910) mesh as a dural substitute, J. Neurosurg., 1985, 63(3): 448-452.

Meddings et al., Collagen vicryl—a new dural prosthesis, Acta Neurochir., 1992, 117(1-2): 53-58.

Pietrucha, K., New collagen implant as dural substitute, Biomaterials, 1991, 12: 320-323.

Sakas et al., Biologically inert synthetic dural substitutes, Appraisal of a medical-grade aliphatic polyurethane and a polysiloxane-carbonate block copolymer, J. Neurosurg., 1990, 73(6): 936-941.

San-Galli et al., Use of a biodegradable elastin-fibrin material, Neuroplast, as a dural substitute, Biomaterials, 1996, 17(11): 1081-1085.

Thompson et al., Silastic dural substitute: experience of its use in spinal and foramen magnum surgery, Br. J. Neurosurg., 1994, 8(2): 157-167.

Yamada et al., Development of a dural substitute from synthetic bioabsorbable polymers, J. Neurosurg., 1997, 86(6): 1012-1017.

Yamagata et al., Clinical experience with expanded polytetrafluoroethylene sheet used as an artificial dura mater, Neurol Med Chir., 1993, 33(8): 582-585.

Bhatt et al., Experimental transplantation of human retinal pigment epithelial cells on collagen substrates., Am. J. Ophthalmol., 1994, 117: 214-221.

Hadlock et al., Ocular cell monolayers cultured on biodegradable substrates, Tissue Eng., 1999, 5: 187-196.

Hartmann et al., Human and porcine anterior lens capsule as support for growing and grafting retinal pigment epithelium and iris pigment epithelium, Graefe3 s Arch Clin Exp Ophthalmol., 1999, 237: 940-945.

Huang et al., Preparation and transplantation of photoreceptor sheets, Current Eye Res., 1998, 17: 573-585.

Lu et al., Retinal pigment epithelial cell adhesion on novel micropatterned surfaces fabricated from synthetic biodegradable polymers, Biomaterials, 2001, 22: 291-297.

Lu et al., Retinal pigment epithelium cell culture on thin biodegradable poly(DL-lactic-co-glycolic acid) films, J Biomater Sci Polymer Ed, 1998, 9: 1187-1205.

Mohay et al., Transplantation of corneal endothelial cells using a cell carrier device, Cornea 1994, 13(2): 173-182.

Nakamura, T. et al., Tumorigenicity of poly-L-lactide (PLLA) plates compared with medical-grade polyethylene, J Biomed mater res., 1994, 28: 17-25.

Oganesian et al., A new model of retinal pigment epithelium transplantation with microspheres, Arch Ophthalmol, 1999, 117: 1192-1200.

(Continued)

*Primary Examiner*—Sandra Saucier
*Assistant Examiner*—Susan Hanley
(74) *Attorney, Agent, or Firm*—Buchanan Ingersoll & Rooney PC

(57) ABSTRACT

The invention disclosed is a hydrogel composition for use as dural substitute, for wound closure of cleft palate and regeneration, and as substrate for cell delivery to the eye. The hydrogel is made of a copolymer of (a) an N-substituted (meth)acrylamide, and (b) a hydroxyalkyl (meth)acrylate, which is covalently crosslinked with dimethacrylate monomers. The swollen gel is in the form of a sheet or membrane that is readily sterilisable, being homogeneous or heterogeneous, non-degradable, non resorbable, elastically deformable, and has an equilibrium water content of at least 50%.

16 Claims, No Drawings

OTHER PUBLICATIONS

Pistner et al., Poly(L-lactide): a long-term degradation study in vivo, Biomat., 1993, 14: 671-677.

Tezel et al., Fate of human retinal pigment epithelial cells seeded onto layers of human Bruch's membrane, Inv. Ophthalmol. & Visual Sci., 1999, 40(2): 467-476.

O'Neill et al., Use of a porcine dermis as a dural substitute in 72 patients, J. Neurosurg., 1984, 61: 351-354.

Gudmundsson et a., Complications to the use of Vicryl-Collagen Dural Substitute, Acta Neurochir, 1995, 132 : 145-147.

Keller et al., Repair of spinal dural defects with vicryl (polyglactin 910) mesh, Journal of spinal disorders, 1989, 2 (2) : 87-92.

Cohen et al., Inflammatory reaction to synthetic dural substitute, J. Neurosurg. 1989, 70 : 633-635.

* cited by examiner

HYDROGEL MEMBRANE COMPOSITION AND USE THEREOF

BACKGROUND OF INVENTION (a) Field of Invention

This invention relates to the preparation of non-degradable hydrogel membranes that form polymer networks swollen in water and are suitable for organ restoration or replacement. The invention also relates to hydrogel systems consisting of a crosslinked network of hydrophilic co-polymers swollen in water or in biological fluids, which are well tolerated by living tissues and can be used in a wide range of biomedical applications. The invention also relates to hydrogels which show dimensional integrity with a water content between 50 and 88%, and viscoelastic properties similar to biological tissues, and which, because of their ability to retain a substantial amount of water with respect to network density, allow the transport of small molecules and nutrients. In addition, the invention also relates to porous hydrogels having low interfacial tension with biological fluids, and structural stability which make them suitable for implantation in soft tissue and in contact with biological fluids such as the cerebrospinal fluid or the blood. The present invention also relates to the use of the above hydrogel membranes to replace or restore the dural membrane when surgical removal of part thereof is needed after traumatic, neoplastic, inflammatory destruction or to correct a congenital defect. It is also useful for wound closure of the palate cleft and regeneration of the defect which aid in the healing of the tissue palate, and for delivery of cells to the eye when part of the cornea or the retina need to be restored.

(b) Description of Prior Art

1—Dura Mater

Dura mater is a membrane, which is found between the skull and the brain. It is also present between the vertebral column and the spinal cord, where it ensures protection against leakage of the cerebrospinal fluid (CSF). Any defect of the dura mater can produce undesirable consequences such as brain herniation, adhesion formation between the neural tissue and the overlying structures, pseudomeningocele, cortical scarring, CSF fistulas and wound infection with potential propagation to the brain parenchyma. Dural defect often requires a dural substitute when there is insufficient dura, for example when a large defect is created in the dural envelope for example in the course of tumour removal. Also, congenital anomalies such as Arnold Chiari malformation and myelomeningoceles and spinal dysraphic states may require a duraplasty as part of the repair. Therefore there is a need to repair such defect with a membrane that can mimic the functionality characteristics of the dura mater and that meets surgical need requirements such as sterile and suturable conditions.

Methods have been developed as an attempt to achieve an efficient closure of dural defect that include various materials selected from the following categories: (i) autologous tissues and allografs and xenografts including viable and nonviable membranes comprising fascia lata, pericranium, temporalis fascia, allantoic membrane, amnioplastin, cartilage membrane, cat gut, lyophilized human cadaver; (ii) alloplastic materials that include metalllic materials comprising aluminium foil, gold foil, nickel plate, platinum foil, silver foil, stainless-steel plate, tantalum; (iii) resorbable materials comprising biological polymers such as collagen, alone or complexed with α-hydroxy acids or methacrylate polymers, elastin-fibrin materials, and synthetic copolymers derived from α-hydroxy acids (iv) non resorbable polymers such as aliphatic polyurethane and polytetrafluoroethylene and polysiloxane-carbonate block copolymer; (v) lattice work of knitted monofilament polypropylene mesh, polyester and silicon composites.

In category (i) according to U.S. Pat. No. 4,400,833, a dural patch is described which utilise heterogeneous animal tissue comprising tendon or ligaments from cow or other animal. Also, in J. Neurosurg 61, 351 (1984) there is disclosed the use of a porcine dermis as a dural substitute. The major drawback of such material is health hazard due to the risk that that animal tissue may vehicle viral agents or prions disease such as Creutzfeld-Jakob disease or bovine spongiform encephalopathy as previously reported. In addition, these materials may create adhesions as a result of severe inflammatory response, and therefore are not safe for human use. Dural substitutes of category (ii) have been used in the past century but are no more used because of their inadequacy and since polymeric materials are preferred with the advance in new biomaterial polymers for artificial organs.

In category (iii) U.S. Pat. No. 5,997,895, relates to a collagen matrix to be used as dural substitutes and in U.S. Pat. No. 5,861,034 a bioabsorbable artificial dura mater is described which is made of lactic acid and ε-caprolactone. Both Patents disclose a non-stable dural substitute that degrade in vivo, and this is characterised by a persistent acute inflammation at 2 weeks. In particular, collagen induces an acute inflammation and a foreign body reaction that leads to a granulation tissue. This inconvenience may necessitates a second operation for tissue removal, cleaning and restoration of the defect. Degradation of poly(lactic acid) proceeds by autocatalytic hydrolysis of unstable functional group, e.g., ester groups, that causes the release of low molecular weight oligomeric products, in contact with the neural parenchyma and bone skull, as well as in the CSF and in the systemic circulation. Ultimately their accumulation in various organs of the body may cause some form of organ failure (e.g. kidneys) over a long period of time. In addition, the degradation causes local nonbacterial inflammatory reactions with activation of macrophage and foreign body giant cells. As a result, the device loses the structural integrity which is associated with its primary function, and therefore its functional integrity. Finally, since various factors influence the rate of degradation of biodegradable polymers, such as pH, ionic strength and the pressure of the environment, and also the geometry and dimension of the device, the rate of degradation and the subsequent rate of production of debris products cannot be controlled after implantation, and consequently the performance of the device cannot be controlled.

However, most of studies are not extensive enough for an appraisal of long term evaluation of degradation of poly (a-hydroxy acids) since the phenomenon of foreign-body tumorigenesis has been observed in rodents after 24 months [Nakumara et al., 1994; Pistner et al., 1994]

In category (i) according to U.S. Pat. No. 4,400,833, a dural patch is described which utilise heterogeneous animal tissue comprising tendon or ligaments from cow or other animal. Also, in J. Neurosurg 61, 351 (1984) there is disclosed the use of a porcine dermis as a dural substitute. The major drawback of such material is health hazard due to the risk that animal tissue may vehicle viral agents or prions disease such as Creutzfeld-Jakob disease or bovine spongiform encephalopathy as previously reported. In addition, these materials may create adhesions as a result of severe inflammatory response, and therefore are not safe for human use. Dural substitutes of category (ii) have been used in the past century but are no more used because of their inadequacy and since polymeric materials are preferred with the advance in new biomaterial polymers for artificial organs.

Dural substitutes of category (iv) are formed of elastomeric materials that eventually may induce formation of neomembranes and are usually sterilized with ethylene oxide gas that can leave residual toxicity. In addition, a problem of watertight has been reported with elastomeric material for dural closure.

Therefore an entirely satisfactory dural substitute remains to be developed. In order to establish an efficient, reliable and safe method for dura augmentation and replacement, the substitute should be non-toxic, non-absorbable, non-resorbable, biologically and chemically inert it should not induce revitalisation of the implant by the surrounding tissues, it should be non adherent to the underlying neural tissue, non irritative, and resistant to ingress of infections. In addition, it should be readily sterilized preferably by autoclave as other currently used methods may lead to changes in properties (toxic residual ethylene oxide) and structures (radio-induced chemical changes), handled and suturable and achieve a watertight closure with the healthy dura mater. It should also be pliable and easy to cut to any specified dimensions and conform easily to the surface of the brain or spinal cord. It should have a high tensile stress or strength and be suturable. It should not support cell adherence, ingrowth and proliferation and remain independent from the neural tissue. It should also provide an effective barrier for the wound against exogenous micro-organisms. It should be manufactured as mass marketable.

2—Palate Cleft

Palate clefts are congenital malformations of the palate due to a failure of the lateral palatine processes to fuse with each other, with the nasal septum, and/or with the posterior margin of the median palatine process.

Surgical treatment of palate clefts (palatoplasty) is a major surgery, which necessitates the isolation of the mucoperioteal flaps of the lateral palate to close the defect. This leads to the formation of important scars, which subsequently impede the normal development of the superior maxillary. This, in turn, causes a pseudoprognathism, which necessitates a major orthodontic treatment. Therefore there is a need to develop an effective method to substitute the classical methods of palatoplasty surgery which aims at correcting the tissue defect of the palate without impeding the normal development of the superior maxillary, and at reducing or preventing scar formation with restoration of velopharyngeal function. The use of an hydrogel membrane to correct the palate cleft hold great promise as a means of creating prosthetic materials since, on the one hand, it allows the closure of the tissue defect and, on the other hand, it provides a polymeric template to guide mesenchymal cells of the tissue palate for in situ repair of the defect during the development of the craniofacial skeleton.

3—Substrate for Cell Delivery to the Eye

Description of Prior Art

The retina which comprises about 150 millions cells is a neural membrane which transmits light stimuli to the brain via several neuronal pathways and relays. The transduction process into which light stimuli are transformed in nerve impulses (action potentials) which are carried to the optical nerve involves several classes of cells organized in layers and that comprises layers of rods and cones, horizontal, bipolar and amacrine cells and a layer of ganglion cells. The retina proper includes three layers of neurones: (a) rods and cones, (b) bipolar cells, and (c) ganglion cells. Light reaches the stratum opticum first and after traversing all the other layers affects the rods and cones in the outermost layer. The nerve impulse which results from the stimulation of the photoreceptors of the retina then passes through the layers in the numerical order given above up to the ganglion cells which form the terminus of the optic nerve. The optical nerve transmits the signal to the lateral geneculate nucleus, which then transmits it to the occipital lobe of the brain. The central part of the retina is the macula lutea and at the centre of the macula there is the fovea centralis (about 1.75 $mm^2$) where conditions for photopic vision are optimum and the highest visual resolution takes place.

Some cause of visual loss include age related macular degeneration (ARMD) which is associated with dysfunction of the retinal pigment epithelial (RPE). The RPE is a monolayer of tightly coupled epithelia cells at the outer layer of the retina. The RPE cells maintain the health of the photosensitive cells of the retina by controlling the flux of electrolytes and small molecules between the blood and the neural retina. Therefore, the disappearance or the dysfunction of RPE results in photosensitive cell death. To overcome this and to rescue photoreceptor cells, one treatment option for maintenance or restoration of retinal function, consists in transplantation of RPE cells as a monolayer beneath the retina to replace the defective cell monolayer. To achieve this, a substrate material is essential to ensure that the RPE cells are in correct polarity with respect to one another and to the photosensitive cells of the retina in order to maintain tissue-specific organisational features after transplantation. In addition, the substrate should be handled by the surgeon without damage to the cells and should have a size to fit the defective zone. Prior to transplantation, the RPE cells must be seeded onto the substrate materials. This procedure allows to verify the viability of cells.

Thus, various substrates have been used in an attempt to attach and hold together RPE cells and to deliver RPE cells to the retina. Anterior lens capsule [Hartman et al., 1999], collagen [Bhatt et al., 1994], gelatin [Huang et al., 1998], fibrinogen [Oganesian et al., 1999], Bruch's membrane [Tezel et al., 1999], biodegradable polymers such as poly-L-lactic acid and poly-lactic-co-glycolic acid) [Hadlock et al., 1999; Lu et al., 1998 and 2001] have been used as carriers to transplant RPE cell monolayers. However these substrates are not suitable in a biological and surgical perspective, principally because they are not biostable after transplantation and they degrade and resorbe over time, releasing low molecular weight oligomeric products, which in turn may cause a retinopathy. In addition this causes the migration of the cell graft away from the site of transplantation. These substrates are also difficult to handle by the surgeon without risk of damage of the carrier device. In addition, those being of biological origin may induce immune rejection after antigen exposure, which cause failure of the graft.

As an alternative to eliminate these problems, there is a nee for a biostable, non-degradable, semi-rigid hydrogel membrane amenable to manipulation during surgical implantation of crosslinked synthetic polymers, of about 30-60 microns thickness with cell adhesivity properties which can be used as a support and proliferation for RPE cells. Through a pars plana sclerotomy into the posterior portion of the eye, this hydrogel-cell hybrid implant could be inserted into the subretinal space via a small retinotomy. Neural retinal cells can also be seeded onto such hydrogel susbtrate for transplantation and restoration of retinal function. Ultimately, the use of such a hydrogel would provide a reliable substrate for coseeding both RPE and retinal cells and then induction in vitro of a biohybrid retinal substitute for the remplacement of the part of the retina. The cells can be obtained either from the patient using a retinal flap in the para- or perifoveal region, from a donor (embryonic retinal cells) or from an established cell culture lines Corneal endothelium cells cover the front of the cornea and maintain the cornea as a transparent refracting surface. Dysfunctional corneal endothelium results in corneal opacification and decreased vision. The treatment is the transplantation of the whole cornea (keratoplasty). However, an alternative approach would be to replace only the functional part of the cornea, i.e., the endothelial monolayer. This could be achieved by seeding corneal endothelial cells onto an artificial substrate for subsequent replacement of defective parts of the cornea. The cells can be obtained either from the patient, from a donor or from established cell culture lines.

Various approaches have been proposed to transplant corneal epithelium such as cell monolayer on a cross-linked gelatine membrane [McCulley et al. 1980]. But gelatine, which is composed of denatured collagen, may undergo biodegradation in vivo and resorption that may lead to complications and infection, as well as the lost of the graft.

SUMMARY OF THE INVENTION

In order to address the foregoing deficiencies of the prior art, there is provided a non-degradable crosslinked polymer compositions comprising synthetic polymers and method to coat surfaces with adhesion-promoting peptides for enhancing adhesion with cells, for applications in neurosurgery, maxillofacial reparative surgery and eye surgery.

It is an object of the present invention to prevent drawbacks of the prior art by using a non-biological prosthetic device that is a non-degradable copolymer hydrogel that can be used safely and efficiently to act as a dural substitute.

It is another object of the invention to provide a copolymer hydrogel membrane that contains at least 50% of water and which promotes exchanges with the physiological environment It is still another object of the invention to provide a copolymer hydrogel that can be autoclaved so as to prevent using a material that may carry infectious agents.

It is another object of the invention to provide an hydrogel that can be sterilized in an autoclave, avoiding ethylene oxide gas sterilisation or gamma irradiation, which could both induce changes in properties and structure of the prosthetic material.

It is an object of this invention to provide an hydrogel sheet or strip variety, which is flexible and pliable.

It is an object of this invention to provide a dural substitute, which is a swollen gel sufficiently transparent to view the underlying neural tissue It is an object of the invention to provide a dural substitute that is suturable and non-degradable, and with superior mechanical biocompatibility and modulus of elasticity close to the native dura mater.

It is still another object of the invention to provide a hydrogel membrane that can be sutured to the defect margins to achieve a watertight closure.

It is yet another object of the invention to provide a method for preparing a physiologically compatible hydrogel membrane of desired thickness, strength and transparency It is another object of the invention to provide a hydrogel membrane that can be used to close primarily the cleft palate and that can support cell ingrowth for subsequent closure of the defect.

It is another object of the invention to provide a method for preparing such hydrogel membrane with the desired properties for cell ingrowth and proliferation, tissue adhesivity and surgical manipulation.

It is an object of the present invention to use a hydrogel membrane than can be coated with cell-adhesion peptides.

It is still an object of the invention to provide an hydrogel membrane with adhesive properties as a substrate for delivery cells to the eye in monolayer for replacing cell monolayers in the eye with tissue cultured cells grown on hydrogels.

It is another object of the invention to transplant RPE cells grown on hydrogel substrate to replace part of the retina of the eye.

It is another object to the invention to transplant corneal endothelium cells grown on the hydrogel substrate according to the intention to replace part of the cornea of the eye.

The invention relates to hydrogels that form a polymer system of cross-linked copolymer chains that contain a significant amount of water for therapeutic use and which are prepared in the form of membranes with variable thickness depending on extended use and which can vary from 30 μm to 700 μm.

More specifically, the invention relates to a hydrogel comprising a cross-linked copolymer of an N-substituted (meth) acrylamide, and a hydroxyalkyl (meth)acrylate. This copolymer is particularly useful for use as a membrane for treating dura mater, palate cleft and cell delivery to the eyes.

DESCRIPTION OF PREFERRED EMBODIMENTS

According to a preferred embodiment of the present invention, there is provided a hydrophilic gel that comprise (a) an N-substituted (meth)acrylamide such as N-monoalkyl or monohydroxyalkyl and N,N-dialkyl (meth) acrylamide of the general formula:

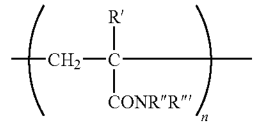

wherein R' is H or $CH_3$ and if R' is H, R" is H or is an alkyl chain with $C_{1-4}$ carbon atoms, and R"' is H or an alkyl chain with $C_{1-6}$ carbon atoms, and if R' is $CH_3$, R" is H or an alkyl group $C_{1-6}$ and R"' is H or is an alkyl chain with $C_{1-18}$ with 1 to 3 OH groups;

(b) a monohydroxyalkyl (meth)acrylate in which the alkyl group has one to six carbon atoms, and (c) a cross-linking agent such as glycol dimethacrylate with one ethylene group or polyethylene glycol dimethacrylate, or other glycol dimethacrylate monomers, and the like.

In a preferred embodiment of the present invention, the reaction mixture consists of from 12 to 22 parts by weight of N-2-hydroxypropyl methacrylamide (HPMA), 20 to 30 parts by weight of a member selected from the group consisting of an monohydroxyalkyl methacrylate, such as 2-hydroxyethyl methacrylate (HEMA), and from 3 to 10 parts by weight of di(meth)acrylate i.e. diester of acrylic acid or methacrylic acid. The polymerization is preferably initiated with any of the known water-soluble radical initiator catalyts that form a redox system that may generate free radicals in aqueous systems and that comprises an inorganic oxidizing agent as an initiator and an inorganic reducing agent as an activator.

These include ammonium persulfate and sodium metabisulfite, or ammonium persulfate and ascorbic acid, or ammonium persulfate and sodium thiosulfate, or sodium monopersulfate and ascorbic acid, or sodium percarbonate and ascorbic acid, and other water soluble hydrogen peroxide generators. The catalysts are added in a proportion in amounts of about 0.3 to 2% by weight to achieve a suitable rate of polymerization and a high monomer conversion leading to the simultaneous formation of copolymer chains and crosslinks.

The polymerization of the above mentioned monomers (a), (b) and (c) is advantageously carried out in the presence of solvent, such as in a mixture of ethylene glycol/water or acetone/water, distilled water being preferred, in a volume ratio of 35 to 49% of solute, preferably in a volume ratio of 42%. Acetone being a water-miscible organic diluent, which has a low chain transfer constant leads to higher yields and higher quality products. The polymerization reaction mixture is purged from oxygen with purified nitrogen. Polymerization is carried out at temperatures of 30° C. to about 60° C., preferably at temperatures of 35° C. to about 55° C. for 12 hours. The hydrogel possesses an equilibrium water content of at least about 50% and is substantially transparent or translucent although capable of being made opaque. The hydrogel is readily pliable without breaking and has strong adhesive properties with living tissues.

In the case where the hydrogel substrate is designed for promoting cell attachment and cell migration, as for example for reconstruction of the cleft palate or for seeding the hydrogel with cells, a N-methacrylolated oligopeptide spacer arm carrying the RGD sequence(arginine-glycine-aspartic acid), such as methacryloylglycylglycylargynyl-glycylaspartic acid, is added to the reacting mixture at a concentration of 0.5 mol% or less. Other peptides that are known to promote cell attachment can also be used via an oligopeptide spacer arm, and may also include, but are not limited to, RGDS (arginine-glycine-aspartic acid-serine)(SEQ ID NO: 1), the pentapetide TYIGSR (Tyr-Ile-Gly-Ser-Arg) (SEQ ID NO:2)or IKVAV (Ile-Lys-Val-Ala-Val) (SEQ ID NO:3). Also, N-acetyl neuraminic acid-HPMA conjugates, such as 2-[1 methyl-2-methacryloyamidoethyl]5-acetamido 3,5-dideoxy-D-glycero-α-D-galacto-2-monulopyranosidonic acid, in the bioactive configuration (RS) may be added to the mixture to promote cell attachement in a concentration of 0.1 to 0.005 mol %. Neuraminic acid is part of cell adhesion molecules and play a major role in cell adhesion.

After transferring the polymerization mixture into moulds consisting of two plates covered with a layer of polypropylene separated by a silicone rubber seal of desired thickness, the polymerization may, for example, be carried out at 35° C. for 6 h. Depending on molar ratio of (a) and (b) and (c), and the ratio of solvent to monomers, hydrogels can be produced with properties suitable for the above mentioned medical applications.

For instance, mechanical properties, adhesivity and porosity can be adjusted by varying the initial composition of the polymerization mixture and the condition of the reaction such as the temperature and the polymer-solvent interactions, leading to either homogeneous or heterogeneous hydrogels.

In addition, the thickness of the hydrogel membrane also governs also properties such as pliability and pseudoelasticity, i.e., the membrane returns to its original shape after the applied force is removed. These properties need to be adapted for the specific application and this can be achieved by varying the thickness of the silicone rubber seal of the mould. The degree of swelling is a function of the concentration of poly-HPMA in the hydrogel with respect to the concentration of the crosslinker and the amount of solvent, while strength and resistance depend primarily on the concentration of poly-HEMA in the formed hydrogel.

After polymerization, the hydrogels are removed from the moulds and washed in distilled water for 24 hours and allowed to equilibrate in distilled water for 1 week.

EXAMPLES

The invention is further illustrated by means of the foiling non limiting examples.

Example 1

In a glass ampoule there was dissolved 0.136 grams of HEMA, 0.15 grams of HPMA and 0.0446 grams of ethylene glycol dimethacrylate (EGDMA) in 0.28 grams of water/ethylene glycol (1:1 wt/wt) by heating and stirring until dissolution. To the resultant solution there was added a redox system made of 0.0273 grams of 6% w/w ammonium persulfate and 0.0273 grams of 12% w/w sodium thiosulfate. The reaction mixture was degassed with pure nitrogen for 5 minutes, thoroughly homogenised and injected using a syringe into moulds having two pre-heated plates that are pre-heated with an internal system of circulating water connected to a thermostated water-bath, each plate being provided with a separation layer made of polypropylene. Care was taken not to introduce air bubbles into the reaction mixture during loading the space of the moulds. The thickness of the gel membrane that is required for the desired application was controlled by the thickness of a distance insert made of silicone rubber that is placed between the two heated plates. Polymerization was carried out at 35° C. for 6 hours.

After polymerization, the gels were allowed to swell in distilled water and were either opaque or transparent depending on the proportion and the composition of the solvent with respect to the monomer concentration. After polymerization, the hydrogels were removed from the moulds and washed in distilled water for 24 hours. Before application, the hydrogel was sterilised in an autoclave at 121 ° C. for 30 minutes.

Example 2

The mixture is the same as in Example 1 except that o.08 mol % of methacrylamide-glycine-glycine-arginine-glycine-aspartic acid was added to increase the adhesivity of the polymer substrate. Polymerization was carried as in Example 1 and after the reaction, the procedure was carried out as in Example 1.

Example 3

A glass ampoule was charged with 0.318 grams of HEMA, 0.15 grams of HPMA, 0.0745 grams of EGDMA, 0.23 grams of water, 0.26 grams of ethylene glycol, 0.0455 grams of 6% w/w ammonium persulfate and 0.0455 grams of 12% w/w sodium thiosulfate. Further procedure is identical to Example 1.

Example 4

The mixture is the same as in Example 3 except that 0.111 grams of EGDMA was used. Polymerization and further procedure are the same as in Example 1.

Example 5

The mixture is the same as in Example 3 except that 0.364 grams of HEMA, 0.082 grams of EGDMA, 0.25 grams of water and 0.28 grams of ethylene glycol were used.

Polymerization was carried as in Example 1.

Example 6

The mixture is the same as in Example 5 except that 0.041 grams of EGDMA, 0.05 grams of ammonium persulfate and 0.05 grams of sodium metabisulfite were used.

Polymerization was carried out as in Example 1.

Example 7

The mixture is the same as in Example 6 except that 0.061 grams of EGDMA was used. The same procedure of polymerization was followed.

Example 8

The mixture consists of 50% by weight of HPMA, 50% by weight of HEMA in distilled water with a weight ratio of 40% in the final volume of the reaction mixture, and was crosslinked with 1 mol % of diethylene glycol dimethacrylate. The mixture was bubbled through with nitrogen and was injected into molds. Polymerization was carried out with 2% by weight of the mixture of monomers, of ammonium persulfate and ascorbic acid at 35° C. for 6 hours.

Example 9

The monomer mixture comprises 30% by weight HPMA, 70% by weight HEMA in distilled water for a weight ratio of 40% to the final volume of the reacting mixture, and 2 mol % of diethylene glycol dimethacrylate. Polymerization was carried as in Example 8.

Example 10

The mixture according to Example 9 was adjusted to 35% by weight of the monomer mixture to the final volume of the reaction mixture and was polymerized in distilled water/acetone in a 1:1 (v/v) ratio. Polymerization was carried as in Example 8.

Example 11

The mixture according to Example 9 was dissolved in distilled water/acetone (40:60, v/v). Polymerization was carried as in Example 8.

Example 12

The mixture according to Example 9 was adjusted to a weight ratio of 30% by weight to the final volume of the reaction mixture with 2 mol % of diethylene glycol dimethacrylate in distilled water/acetone (70:30, v/v).

Polymerization was carried as in Example 8.

Example 13

The mixture is the same as in Example 12 except that 2 mol % of triethylene glycol dimethacrylate was used.

Polymerization was carried as in Example 8.

Example 14

The mixture according to Example 12 was disolved and polymerized in distilled water. Polymerization was carried as in Example 8.

Example 15

Poly (HPMA-co-HEMA) hydrogels membranes of 100 μm thickness were successfully used to replace the dura mater in the adult and neonatal rat, and in the cat after a laminectomy was performed and with the removal of part of the dura mater.

A pathological analysis after several months shows:

no inflammatory reaction of the spinal cord or surrounding mesenchymal tissue no neuro-membranous adhesions no calcification or ossification no degradation of the polymer permanent stationary position Example 16

RPE cells were cultured onto poly (HPMA-co-HEMA) hydrogel membranes in DMEM containing 10% fetal bovine serum at a density of 6×105 cell/ml. Poly (HPMA-co-HEMA) hydrogel membranes were conditioned with a surface active agent containing the RGD peptide to promote cell attachment and growth. Viability of cells and differentiation were assessed by Trypan Blue exclusion. RPE cells attach readily to the hydrogel substrates and proliferate to form monolayers of polygonal epitheloid cells with a viability equal to or above 90%.

Although the invention has been described with reference to specific embodiments, it is understood that modifications are possible without departing from the scope and spirit of the invention, as defined in the appended claims.

The invention claimed is:

1. A hydrogel comprising a cross-linked copolymer prepared by radical polymerization, in an aqueous system, of monomers consisting of a N-substituted methacrylamide, a hydroxyalkyl methacrylate and a cross-linking agent;

wherein said N-substituted methacrylamide is N-monohydroxyalkyl methacrylamide, N-dihydroxyalkyl methacrylamide or N-trihydroxyalkyl methacrylamide; and said hydrogel is homogeneous.

2. The hydrogel according to claim 1, wherein said N-monohydroxyalkyl methacrylamide, N-dihydroxyalkyl methacrylamide or N-trihydroxyalkyl methacrylamide is represented by the following general formula

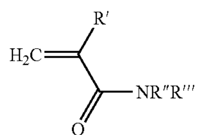

wherein R' is $CH_3$, R" is H or a $C_{1-6}$ alkyl group and R''' is $C_{1-18}$ alkyl group substituted by 1 to 3 OH groups.

3. The hydrogel according to claim 2, wherein said N-substituted (meth)acrylamide is a N-monohydroxyalkyl (meth) acrylamide.

4. The hydrogel according to claim 1, wherein said cross-linked agent is a di(meth)acrylate.

5. The hydrogel according to claim 4, wherein said di(meth)acrylate is ethylene glycol dimethacrylate.

6. The hydrogel according to claim 4, wherein said di(meth)acrylate is a polyethylene glycol di(meth)acrylate.

7. The hydrogel according to claim 1, wherein said N-monohydroxyalkyl methacrylamide is N-2-hydroxypropyl methacrylamide, and said hydroxyalkyl (meth)acrylate is 2-hydroxyethyl methacrylate.

8. The hydrogel according to claim 7, wherein said copolymer is prepared by radical polymerization of 12 to 22 parts by weight of N-2-hydroxypropyl methacrylamide, 20 to 30 parts by weight of 2-hydroxyethyl methacrylate and from 3 to 10 parts by weight of ethylene glycol dimethacrylate.

9. A hydrogel comprising a cross-linked copolymer prepared by radical polymerization, in an aqueous system, of monomers consisting of a N-substituted methacrylamide, a hydroxyalkyl methacrylate, less than 0.2 mol % of a N-methacrylolated oligopeptide spacer arm substituted by a peptide sequence and a cross-linking agent; wherein said N-substituted methacrylamide is N-monohydroxyalkyl methacrylamide, N-dihydroxyalkyl methacrylamide or N-trihydroxyalkyl methacrylamide; and said hydrogel is homogeneous.

10. The hydrogel according to claim 9, wherein said peptide sequence is the RGD sequence (arginine-glycine-aspartic acid).

11. The hydrogel according to claim 9, wherein said peptide sequence is the RGDS sequence (arginine-glycine-aspartic acid-serine) (SEQ ID NO: 1).

12. The hydrogel according to claim 9, wherein said peptide sequence is the pentapeptide TYIGSR sequence (Tyr-Ile-Gly-Ser-Arg) (SEQ ID NO: 2).

13. The hydrogel according to claim 9, wherein said peptide sequence is the IKVAV sequence (Ile-Lys-Val-Ala-Val) (SEQ ID NO: 3).

14. The hydrogel according to claim 1, which comprises 0.1 to 0.005 mol % of N-acetyl neuraminic acid—HPMA conjugates.

15. A hydrogel comprising a cross-linked copolymer prepared by radical polymerization, in an aqueous system, of monomers consisting of a N-substituted methacrylamide, a hydroxyalkyl methacrylate, 0.1 to 0.005 mol % of 2-[1-methyl-1- methacryloyamidoethyl]-5-acetamido 3,5-dideoxy-D-glycero-α-D-galacto-2-monulopyranosidonic acid and a cross-linking agent; wherein said N-substituted methacrylamide is N-monohydroxyalkyl methacrylamide, N-dihydroxyalkyl methacrylamide or N-trihydroxyalkyl methacrylamide: and said hydrogel is homogeneous.

16. A membrane having a thickness between about 30 μm and 700 μm comprising a hydrogel according to claim 1.

* * * * *

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Oligopeptide

<400> SEQUENCE: 1

Arg Gly Asp Ser
1


<210> SEQ ID NO 2
```

-continued

```
<211> LENGTH: 5
<212> TYPE: PRT
<213> ORGANISM: Artificial Sequence
<220> FEATURE:
<223> OTHER INFORMATION: Oligopeptide

<400> SEQUENCE: 2

Tyr Ile Gly Ser Arg
1               5


<210> SEQ ID NO 3
<211> LENGTH: 5
<212> TYPE: PRT
<213> ORGANISM: Artificial Sequence
<220> FEATURE:
<223> OTHER INFORMATION: Oligopeptide

<400> SEQUENCE: 3

Ile Lys Val Ala Val
1               5
```